United States Patent
Smith et al.

(10) Patent No.: US 9,099,863 B2
(45) Date of Patent: Aug. 4, 2015

(54) SURGICAL GENERATOR AND RELATED METHOD FOR MITIGATING OVERCURRENT CONDITIONS

(75) Inventors: Robert B. Smith, Loveland, CO (US); Steven C. Rupp, Arvada, CO (US)

(73) Assignee: Covidien LP, Mansfield, MA (US)

(*) Notice: Subject to any disclaimer, the term of this patent is extended or adjusted under 35 U.S.C. 154(b) by 904 days.

(21) Appl. No.: 13/228,996

(22) Filed: Sep. 9, 2011

(65) Prior Publication Data

US 2013/0066311 A1 Mar. 14, 2013

(51) Int. Cl.
*H02H 3/08* (2006.01)
*A61B 18/12* (2006.01)
*A61B 18/14* (2006.01)
*A61B 18/00* (2006.01)

(52) U.S. Cl.
CPC .............. *H02H 3/08* (2013.01); *A61B 18/1206* (2013.01); *A61B 18/1233* (2013.01); *A61B 18/1402* (2013.01); *A61B 18/1445* (2013.01); *A61B 2018/00642* (2013.01); *A61B 2018/00702* (2013.01); *A61B 2018/00726* (2013.01); *A61B 2018/00827* (2013.01)

(58) Field of Classification Search
CPC ................. H02H 3/08; A61B 18/1233; A61B 2018/00642; A61B 2018/00726; A61B 2018/00827
USPC .................................... 606/32, 34, 35, 38, 42
See application file for complete search history.

(56) References Cited

U.S. PATENT DOCUMENTS

| | | | |
|---|---|---|---|
| 4,559,943 A | 12/1985 | Bowers | |
| 4,586,120 A | 4/1986 | Malik et al. | |
| 4,727,874 A * | 3/1988 | Bowers et al. | 606/38 |
| 4,942,313 A | 7/1990 | Kinzel | |
| 5,318,563 A * | 6/1994 | Malis et al. | 606/38 |
| 5,443,463 A | 8/1995 | Stern et al. | |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

International Search Report issued in corresponding patent application No. PCT/US2012/053619 mailed Mar. 4, 2013.

(Continued)

*Primary Examiner* — George Evanisko

(57) ABSTRACT

A surgical generator and related method for mitigating overcurrent conditions are provided. The surgical generator includes a power supply, a radio frequency output stage, an overcurrent detection circuit in operative communication with an interrupt circuit, and a processor. The power supply generates a power signal and supplies the power signal to the radio frequency output stage. The radio frequency output stage generates a radio frequency signal from the power signal. The overcurrent detection circuit detects an overcurrent of the power signal and/or an overcurrent of the radio frequency signal. The interrupt circuit provides an interrupt signal in response to a detected overcurrent. The processor receives the interrupt signal and supplies a pulse-width modulation signal to the power supply and incrementally decreases the duty cycle of the pulse-width modulation signal in response to the interrupt signal. The radio frequency output stage may be disabled in response to the detected overcurrent.

10 Claims, 7 Drawing Sheets

(56) References Cited

U.S. PATENT DOCUMENTS

| | | | |
|---|---|---|---|
| 5,540,681 | A | 7/1996 | Strul et al. |
| 6,041,260 | A | 3/2000 | Stern et al. |
| 6,142,992 | A | 11/2000 | Cheng et al. |
| 6,235,020 | B1 * | 5/2001 | Cheng et al. ............ 606/34 |
| 6,251,106 | B1 | 6/2001 | Becker et al. |
| 6,398,779 | B1 | 6/2002 | Buysse et al. |
| 6,426,886 | B1 | 7/2002 | Goder |
| 6,464,696 | B1 | 10/2002 | Oyama et al. |
| 6,740,079 | B1 | 5/2004 | Eggers et al. |
| 6,923,804 | B2 | 8/2005 | Eggers et al. |
| 7,041,096 | B2 | 5/2006 | Malis et al. |
| D574,323 | S | 8/2008 | Waaler |
| 2004/0030329 | A1 | 2/2004 | Hagg |
| 2006/0161148 | A1 | 7/2006 | Behnke |
| 2007/0173808 | A1 * | 7/2007 | Goble ............ 606/34 |
| 2008/0281311 | A1 | 11/2008 | Dunning et al. |
| 2010/0063494 | A1 | 3/2010 | Orszulak |
| 2010/0063497 | A1 | 3/2010 | Orszulak |
| 2011/0172656 | A1 | 7/2011 | Schall et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1681026 | 7/2006 |
| EP | 1776929 | 4/2007 |
| EP | 2160992 A2 | 3/2010 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 2154881 | 9/1985 |
| GB | 2164473 | 3/1986 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Pleven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

(56) References Cited

OTHER PUBLICATIONS

Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1: p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
European Search Report issued in corresponding EP application No. 12829715.7 dated Mar. 27, 2015.

* cited by examiner

SURGICAL GENERATOR AND RELATED METHOD FOR MITIGATING OVERCURRENT CONDITIONS

BACKGROUND

1. Technical Field

The present disclosure relates to surgical generators. More particularly, the present disclosure relates to a surgical generator and related method for mitigating overcurrent conditions.

2. Discussion of Related Art

Energy-based tissue treatment is well known in the art. Various types of energy (e.g., electrical, ultrasonic, microwave, cryogenic, heat, laser, etc.) are applied to tissue for surgical treatment. Electrosurgery involves application of high radio frequency electrical current, e.g., electrosurgical energy, to a surgical site to cut, ablate, coagulate, or seal tissue.

In bipolar electrosurgery, there are typically two electrodes disposed on a held-held instrument. One of the electrodes of the hand-held instrument functions as the active electrode and the other as the return electrode. The return electrode is placed in close proximity to the active electrode such that an electrical circuit is formed between the two electrodes (e.g., electrosurgical forceps). Bipolar electrosurgical techniques and instruments can be used to coagulate blood vessels or tissue, e.g., soft tissue structures, such as lung, brain, and intestine. By controlling the intensity, frequency, and duration of the electrosurgical energy applied between the electrodes and through the tissue, a surgeon can cauterize, coagulate, desiccate, seal, or simply reduce or slow bleeding of tissue. In order to achieve one of these desired surgical effects without causing unwanted charring of tissue at the surgical site or causing collateral damage to adjacent tissue from thermal spread, the output from the electrosurgical generator is controlled, such as power, waveform, voltage, current, pulse rate, etc.

In monopolar electrosurgery, the active electrode is typically disposed on the surgical instrument held by the surgeon, and a patient return pad having one or more return electrodes is placed remotely from the active electrode to carry the current back to the generator and safely disperse current applied by the active electrode. The return electrodes usually have a large patient-contact surface area to minimize tissue heating at that site. Heating is caused by high current densities that directly depend on the surface area. A larger surface contact area results in lower localized heat intensity. The size of the return electrodes are chosen based on assumptions of the maximum current utilized during a particular surgical procedure and the duty cycle (i.e., the percentage of time the generator is on).

Another type of energy-based treatment of tissue is microwave-energy based treatment. There are several types of microwave surgical instruments (i.e., microwave probes) in use, e.g., monopole, dipole, and helical. The monopole antenna probe consists of a single, elongated microwave conductor exposed at the end of the probe. A dielectric sleeve typically surrounds the monopole antenna probe. The second type of microwave probe commonly used is the dipole antenna probe, which consists of a coaxial construction having an inner conductor and an outer conductor with a dielectric junction separating a portion of the inner conductor. The inner conductor may be coupled to a portion corresponding to a first dipole-radiating portion, and a portion of the outer conductor may be coupled to a second dipole-radiating portion. The dipole radiating portions may be configured such that one radiating portion is located proximally of the dielectric junction and the other portion is located distally of the dielectric junction. In the monopole and dipole antenna probes, microwave energy generally radiates perpendicularly away from the axis of the conductor.

SUMMARY

According to an aspect of the present disclosure, a method for mitigating overcurrent is provided. The method includes the steps of: supplying a pulse-width modulation signal to a power supply (e.g., a DC-to-DC power supply); generating within the power supply a power signal in response to the pulse-width modulation signal; supplying the power signal to a radio frequency output stage; generating within the radio frequency output stage a radio frequency signal from the power signal; supplying the radio frequency signal to a load; detecting an overcurrent of the power signal and/or the radio frequency signal; sending an interrupt signal to a processor in response to the detected overcurrent; disabling the radio frequency output stage in response to the detected overcurrent; and incrementally decreasing, via the processor, the duty cycle of the pulse-width modulation signal in response to the interrupt signal. The radio frequency signal may be applied to tissue, e.g., electrosurgical energy is applied to tissue.

According to an aspect of the present disclosure, the interrupt signal can cause the processor to execute an interrupt service routine and/or enter into a recovery state. Additionally or alternatively, the processor can disable the radio frequency output stage in response to the overcurrent, e.g., during the interrupt service routine and/or the recovery state. Additionally or alternatively, a cutoff circuit can disable the radio frequency output stage in response to the overcurrent.

According to an aspect of the present disclosure, the radio frequency output stage includes two driving transistors coupled to a transformer in a push-pull configuration. The disabling of the radio frequency output stage may include disabling driving signals to the two driving transistors.

In any of the aspects, a method further includes the steps of: suspending a dz/dt algorithm in response to the detected overcurrent; maintaining, by the processor, a low duty cycle of the pulse-width modulation signal for at least a predetermined time; enabling the radio frequency output stage after the predetermined time; and incrementally increasing, by the processor, the duty cycle of the pulse-width modulation signal after the predetermined time.

According to an aspect of the present disclosure, the processor includes one or more programming instructions defining a control system to control the power supply and an interrupt service routine. The interrupt service routine may include one or more programming instructions to set a setpoint of the control system to maintain a low duty cycle of the pulse-width modulation signal for at least a predetermined time.

According to another aspect of the present disclosure, a surgical generator includes a power supply, a radio frequency output stage, an overcurrent detection circuit, an interrupt circuit, and a processor. The surgical generator may be an electrosurgical generator, a surgical microwave generator, a surgical ultrasonic generator, or the like. The power supply generates a power signal and supplies the power signal to the radio frequency output stage. The radio frequency output stage generates a radio frequency signal from the power signal. The overcurrent detection circuit detects an overcurrent of the power signal and/or an overcurrent of the radio frequency signal. The interrupt circuit is in operative communication with the overcurrent detection circuit and provides an interrupt signal in response to a detected overcurrent. The processor receives the interrupt signal from the interrupt circuit. The processor supplies a pulse-width modulation signal to the power supply and incrementally decreases the duty cycle of the pulse-width modulation signal in response to the interrupt signal. The radio frequency output stage may be disabled in response to the detected overcurrent.

According to another aspect of the present disclosure, the surgical generator includes a cutoff circuit. The cutoff circuit is in operative communication with the overcurrent detection circuit. The cutoff circuit disables the power supply in response to a detected overcurrent from the overcurrent detection circuit. Additionally or alternatively, the processor disables the power supply in response to the interrupt signal. The cutoff circuit and/or the processor can disable the power supply by disabling driving signals to two driving transistors coupled to a transformer in a push-pull configuration.

In any of the aspects, the processor may maintain a low duty cycle of the pulse-width modulation signal for at least a predetermined time. Additionally or alternatively, the processor incrementally increases the duty cycle of the pulse-width modulation signal after the predetermined time and re-enables the radio frequency output stage after the predetermined time.

According to another aspect of the present disclosure, the processor includes one or more programming instructions defining a control system to control the power supply and an interrupt service routine invoked by the interrupt signal. The interrupt service routine includes one or more programming instructions to set a setpoint of the control system to maintain a low duty cycle of the pulse-width modulation signal for at least a predetermined time. The interrupt service routine may also include one or more programming instructions to suspend a dz/dt algorithm in response to the interrupt.

BRIEF DESCRIPTION OF THE DRAWINGS

Objects and features of the presently-disclosed surgical generator and related method for mitigating overcurrent conditions will become apparent to those of ordinary skill in the art when descriptions of various embodiments thereof are read with reference to the accompanying drawings, of which.

DETAILED DESCRIPTION

Figure 1:
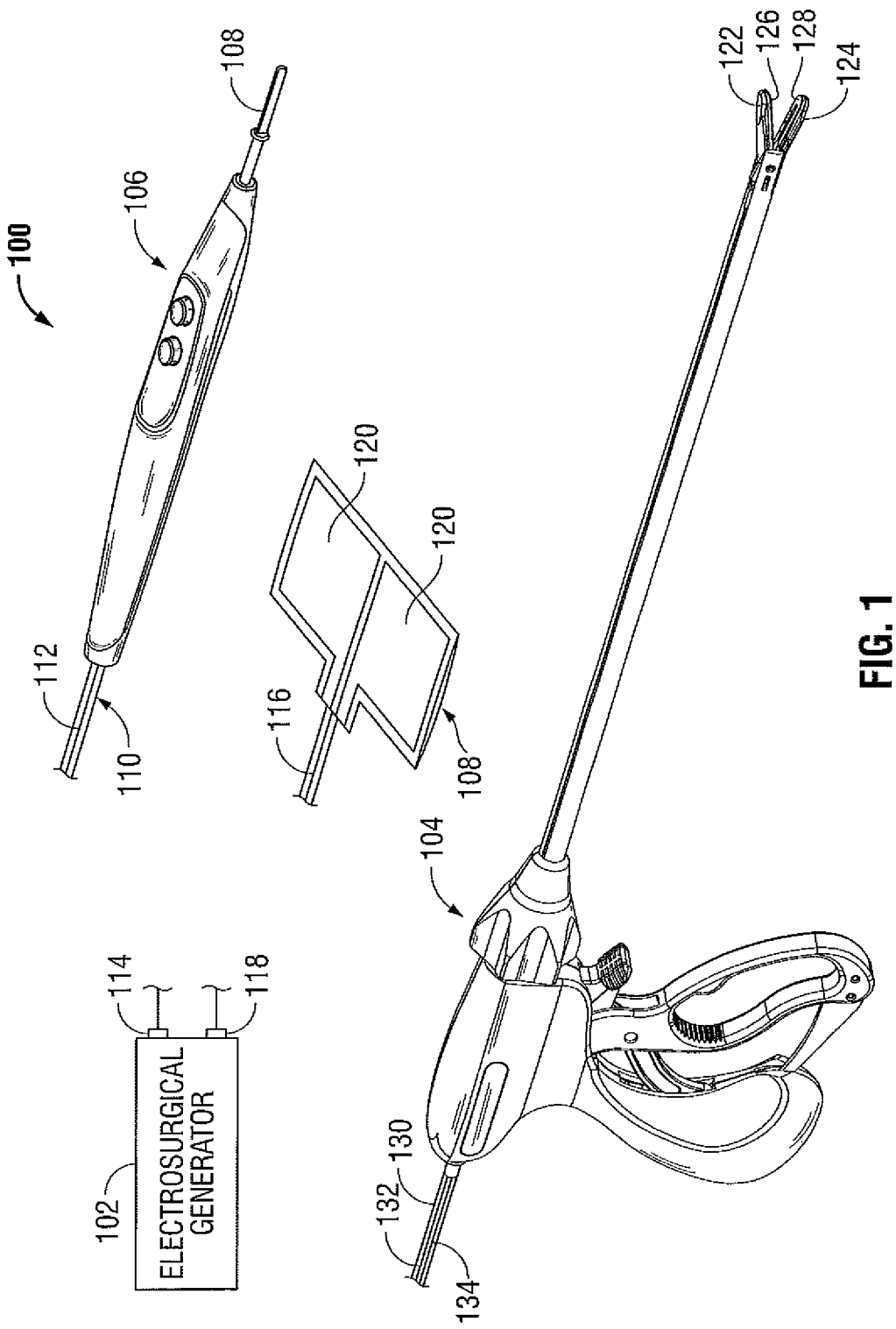
FIG. 1 shows an electrosurgical system for mitigating overcurrent conditions according to an embodiment of the present disclosure.

Hereinafter, embodiments of a surgical generator and related method for mitigating overcurrent conditions of the present disclosure are described with reference to the accompanying drawings. Like reference numerals may refer to similar or identical elements throughout the description of the figures. In the following description, well-known functions or constructions are not described in detail to avoid obscuring the present disclosure in unnecessary detail.

FIG. 1 shows an electrosurgical system 100 according to an embodiment of the present disclosure. The electrosurgical system 100 includes an electrosurgical generator 102, electrosurgical forceps 104, a monopolar electrosurgical instrument 106, and a return pad 108 for returning current to the electrosurgical generator 102 from the monopolar electrosurgical instrument 106. The electrosurgical generator 102 is configured to mitigate overcurrent conditions therewithin as explained in more detail below.

In some of the embodiments, the electrosurgical generator 102 is described as an electrosurgical generator; however, it is to be appreciated that a microwave surgical generator or an ultrasonic surgical generator may be used as the electrosurgical generator 102 where appropriate in the various embodiments disclosed herein.

The electrosurgical generator 102 includes a plurality of outputs for interfacing with various surgical instruments such as electrosurgical instruments, e.g., the electrosurgical forceps 104, the monopolar electrosurgical instrument 106, a footswitch (not shown), etc. Further, the electrosurgical generator 102 includes electronic circuitry configured to generate a radio frequency signal specifically suited for various energy-based surgical procedures such as electrosurgical modes (e.g., cutting, blending, division, etc.) and procedures (e.g., monopolar, bipolar, vessel sealing). For example, the electrosurgical generator 102 supplies electrosurgical energy for application to tissue for vessel sealing using the electrosurgical forceps 104.

The electrosurgical system 100 includes one or more monopolar electrosurgical instruments 106 having one or more electrodes 108 (e.g., electrosurgical cutting probe, ablation electrode(s), etc.) for treating tissue of a patient. The monopolar electrosurgical instrument 106 is coupled to a cable 110 that includes a supply line 112. The electrosurgical generator 102 supplies electrosurgical energy to the monopolar electrosurgical instrument 106 through the supply line 112. The monopolar electrosurgical instrument 106 includes active electrode 108 that is connected via the supply line 112 to an active terminal 114 of the electrosurgical generator 102, allowing the monopolar electrosurgical instrument 106 to coagulate, ablate, and/or otherwise treat tissue. The electrosurgical energy is returned to the electrosurgical generator 102 through the return pad 108 via a return line 116 at a return terminal 118 of the electrosurgical generator 102.

The return pad 108 may include a plurality of return electrodes 120 that are arranged to minimize the chances of undesired tissue heating by maximizing the overall contact area with the patient. In addition, the electrosurgical generator 102 and the return pad 108 may be configured for monitoring so-called "tissue-to-patient" contact to insure that sufficient contact exists therebetween to further minimize chances of tissue damage.

The electrosurgical system 100 also includes electrosurgical forceps 104 for treating tissue of a patient. The electrosurgical forceps 104 includes opposing jaw members 122, 124 having an active electrode 126 and a return electrode 128 disposed therein, respectively. The active electrode 126 and the return electrode 128 are connected to the electrosurgical generator 102 through a cable 130 that includes a supply line 132 and a return line 134 coupled to the active terminal 114 and the return terminal 118, respectively. The electrosurgical forceps 104 is coupled to the electrosurgical generator 102 at a connector having connections to the active terminal 114 and the return terminals 118 (e.g., pins) via a plug disposed at the end of the cable 130, wherein the plug includes contacts from the supply line 132 and the return line 134.

Figure 2:
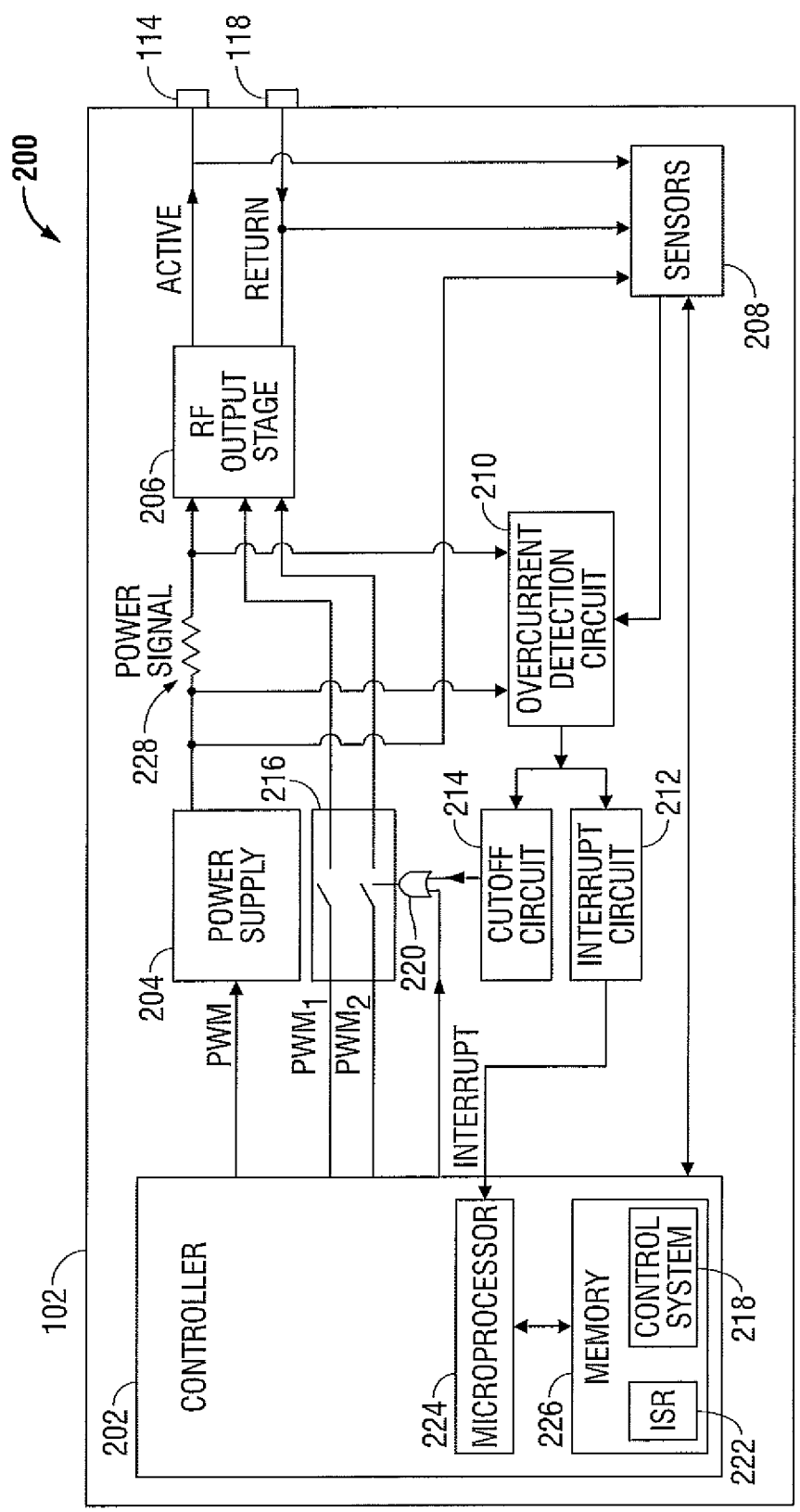
FIG. 2 shows a block diagram of the electrosurgical surgical generator of FIG. 1 for mitigating overcurrent conditions according to an embodiment of the present disclosure.

FIG. 2 shows a block diagram of the electrosurgical surgical generator 102 of FIG. 1 configured to mitigate overcurrent conditions according to an embodiment of the present disclosure. The electrosurgical generator 102 includes a controller 202, a power supply 204, a radio frequency ("RF") output stage 206, sensors 208, an overcurrent detection circuit 210, an interrupt circuit 212, a cutoff circuit 214 and switches 216.

The power supply 204 is connected to an alternating current ("AC") source (e.g., an electrical wall outlet) and provides a power signal to the RF output stage 206; additionally or alternatively, the AC source may be rectified prior to being supplied to the power supply 204. The power signal supplied by the power supply 204 is typically a direct current signal. The RF output stage 206 converts the power signal into a radio frequency signal (e.g., electrosurgical energy) that is provided to the active terminal 114. The electrosurgical energy is returned to the RF output stage 206 via the return terminal 118, e.g., the electrosurgical energy may be returned through a return pad (see FIG. 1). In particular, the RF output stage 206 generates electrosurgical energy having high-energy sinusoidal waveforms. The RF output stage 206 is configured to operate in a plurality of modes, during which the electrosurgical generator 102 outputs electrosurgical energy having corresponding waveforms with specific duty cycles, peak voltages, crest factors, etc.

The power supply 204 may include a DC-to-DC power supply, such as a buck power supply, a boost power supply, a buck-boost power supply, or other suitable switched-mode power supply. The power supply 204 receives a pulse-width-modulated ("PWM") waveform from the controller 202. The duty cycle of the PWM controls the power supply 204, which, in turn, controls the generation of the power signal supplied to the RF output stage 206.

The RF output stage 206 receives two PWM signals from the controller 202. Specifically, the controller 202 supplies PWM1 and PWM2 to the RF output stage 206 to control the generation of the electrosurgical energy. The PWM1 and PWM2 signals may have a 50% duty cycle and may be square waves that are 180° out of phase with respect to each other. The PWM1 and PWM2 signals pass through switches 216 that are configured to either couple the PWM1 and PWM2 signal to the RF output stage 206, or to isolate the signals therefrom.

Figure 3A:
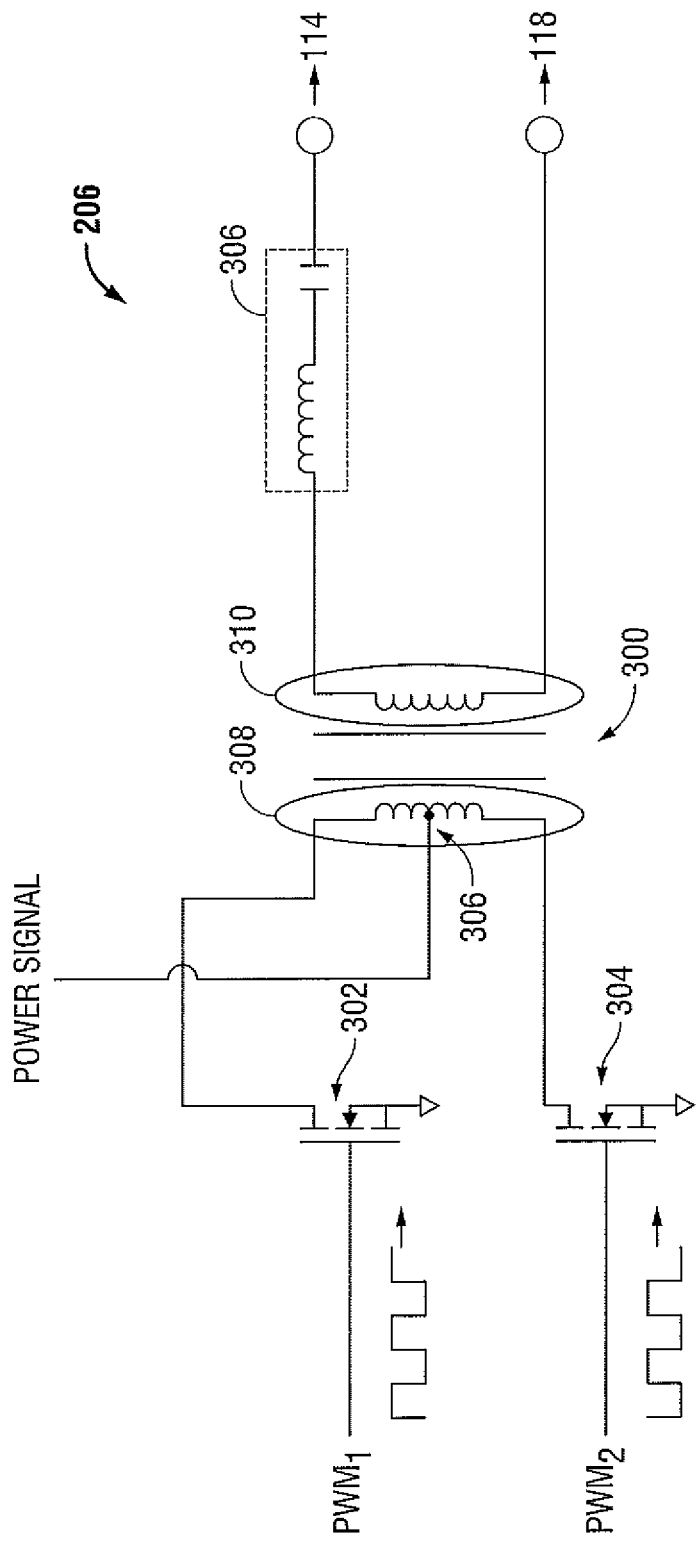
FIG. 3A shows a schematic diagram of the radio frequency output stage of the electrosurgical generator of FIG. 2 according to an embodiment of the present disclosure.

FIG. 3A shows a schematic diagram of the radio frequency output stage 206 of the electrosurgical generator of FIG. 2 according to an embodiment of the present disclosure. The radio frequency output stage 206 includes a transformer 300, transistors 302, 304, and a tank circuit 306. The transformer 300 and the transistors 302, 304 are in a push-pull configuration. The PWM1 signal controls the switching of the transistor 302, and the PWM2 signal controls the switching of the transistor 304. The power signal is fed into the center tap 306 of the primary side 308 of the transformer 300. The power signal is converted to electrosurgical energy on the second side 310 of the transformer 300. The tank circuit 306 filters out frequencies outside of a target frequency band of the electrosurgical energy. That is, the tank circuit 306 is a bandpass filter which allows a predetermined range of frequencies of the electrosurgical energy to pass through to the active terminal 114.

Referring again to FIG. 2, the electrosurgical generator 102 also includes sensors 208. The electrosurgical generator 102 receives feedback from the one or more sensors 208 to form a closed-loop control system 218 (described below) within the controller 202. The one or more sensors 208 measure a variety of tissue and/or energy properties (e.g., tissue impedance, tissue temperature, output current and/or voltage, etc.), and provide feedback to the controller 202. Such sensors may include voltage and current sensors that are coupled to the active and returns terminals 114, 118 of the electrosurgical generator 203. In response to the sensor signals from the one or more sensors 208, the controller 202 controls the power supply 204 and/or the RF output stage 206, which then adjusts the power signal and/or the electrosurgical energy, respectively. The controller 202 also receives input signals from the input controls of the electrosurgical generator 102, the instrument 106 or forceps 104 (see FIG. 1). The controller 202 utilizes the input signals to adjust the electrosurgical energy supplied to the active and return terminals 114, 118 by the electrosurgical generator 102 and/or performs other control functions thereon.

The sensors 208 are also coupled to the overcurrent detection circuit 210. The overcurrent detect circuit 210 receives a current signal that corresponds to the electrosurgical energy current. Additionally or alternatively, the overcurrent detection circuit 210 is coupled to a sense resistor 228 to measure the current of the power signal from the power supply 204. The overcurrent detection circuit 210 can determine the current flowing through the sense resistor 328 by measuring the voltage across the sense resistor 228. The voltage across the sense resistor 228 can be correlated with the current flowing through the sense resistor 228 using Ohm's Law when the resistance of the sense resistor 228 is known or determined. For example, the overcurrent detection circuit 210 receives a voltage signal that, when multiplied by a predetermining constant, is equal to the instantaneous current of the electrosurgical energy supplied to the active terminal 114. The predetermined constant may be the inverse of the resistance of the sense resistor 228, i.e., the conductance of the sense resistor 228.

The overcurrent detection circuit 210 detects when the current of the electrosurgical energy has exceeded a reference value and when the current of the power signal has exceeded another reference value. The overcurrent detection circuit 210 sends a signal to the interrupt circuit 212 and the cutoff circuit 214 when an overcurrent condition exists. In response to the signal from the overcurrent detection circuit 210, the interrupt circuit 212 sends an interrupt signal to the controller 204. Likewise, the cutoff circuit 214 sends a signal to switches 216 to disconnect the PWM1 and PWM2 signals from the controller 202 thereby disabling the RF output stage 206.

Figure 3B:
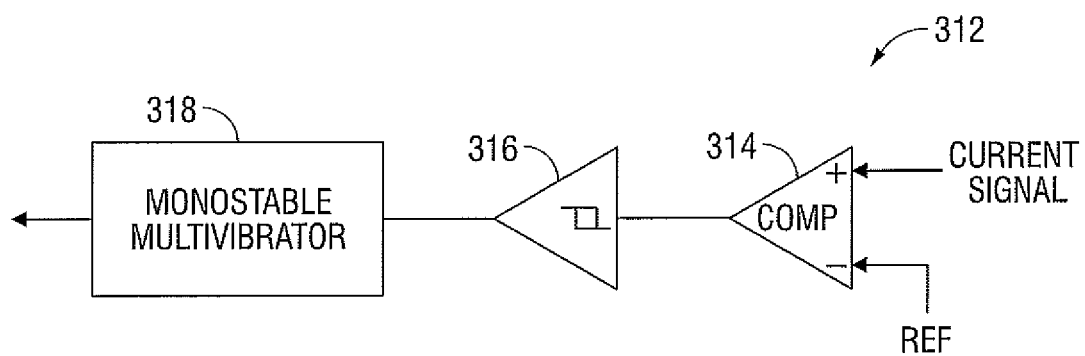
FIG. 3B shows a schematic diagram of the overcurrent detection circuit of the electrosurgical generator of FIG. 2 according to an embodiment of the present disclosure.
Figure 3C:
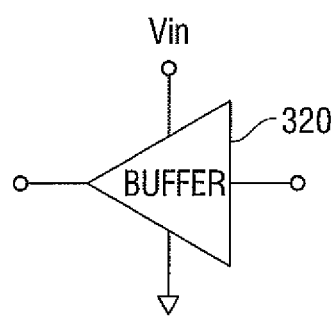
FIG. 3C shows a schematic diagram of a buffer used by the interrupt circuit and the cutoff circuit of the electrosurgical generator of FIG. 2.

Referring now to FIGS. 2, 3B, and 3C. FIG. 3B shows a schematic diagram 312 of the overcurrent detection circuit 210 of the electrosurgical generator of FIG. 2 according to an embodiment of the present disclosure. The overcurrent detection circuit 210 receives a signal representing the current of the electrosurgical energy or the current of the power signal and compares it to a reference using a comparator 314. The output of the comparator 314 is fed into a Schmidt trigger 316, which, in turn, causes a monostable multivibrator 318 to generate a pulse for a predetermined period. The output of the monostable multivibrator 318 is fed into the interrupt circuit 212 and the cutoff circuit 214. FIG. 3C shows a buffer 320. The buffer 320 may be the interrupt circuit 212 and/or the cutoff circuit 214.

Referring again to FIG. 2, when an overcurrent detection circuit 210 detects an overcurrent, a signal is sent to the cutoff circuit 214 which, in response thereto, sends a signal to an input pin of an OR gate 220. The output of the OR gate 220 sends a signal to the switches 216 to disconnect the PWM1 and PWM2 signals from the RF output stage 206.

The interrupt circuit 212 sends an interrupt signal to the controller 202 that causes the interrupt service routine 222 ("ISR") to execute as described below. Additionally or alternatively, the interrupt may cause the controller 202 to enter into a recovery state, e.g., hold one or more other processors in reset.

In some embodiments, in order for the system to recover from an overcurrent event, the software current limit must be set to a level lower than the hardware cycle-by-cycle current limit; otherwise, the overcurrent state machine may constantly be re-entered if the conditions causing the overcurrent remain.

The controller 202 includes a microprocessor 224 in operable communication with a memory 226, which may be volatile type memory (e.g., RAM) and/or non-volatile type memory (e.g., flash media, disk media, etc.). The memory 226 includes one or more instructions including the ISR 222 and the control system 218.

As previously mentioned, the microprocessor 224 includes an output port that is operably connected to the power supply 204 and the RF output stage 206 to allow the microprocessor 224 to control the output of the electrosurgical generator 102 according to either open or closed control loop schemes. Alternatively, the microprocessor 224 may be substituted by other processors (e.g., a control circuit) adapted to perform the calculations discussed herein. Additionally or alternatively, the control system 218 may include one or more PID control loops for controlling the power supply 204 and the RF output stage 206.

Figure 4:
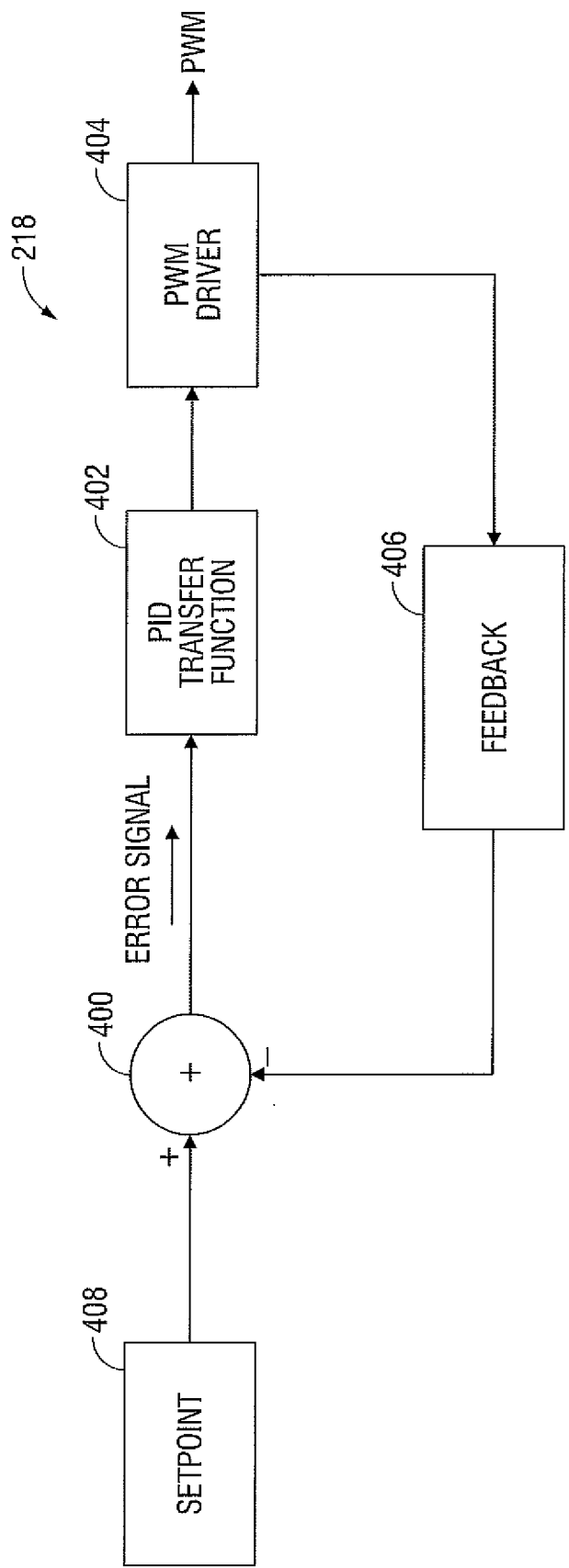
FIG. 4 shows a block diagram of a control system for the electrosurgical generator of FIG. 2 according to an embodiment of the present disclosure.

FIG. 4 shows a block diagram of the control system 218 of the controller 202 for controlling the electrosurgical generator 102 of FIG. 2 according to an embodiment of the present disclosure. The control system 218 includes a summer 400, a PID transfer function 402, a PWM driver 404, a feedback 406 and a setpoint 408.

The summer 400, the PID transfer function 304, the PID transfer function 402, the feedback 406, and the setpoint 408 may be implemented by an operative set of processor executable instructions within memory 226 configured to be executed by at least one processor 224 (see FIG. 2). The memory 226 is a non-transitory computer readable (i.e., readable by microprocessor 224) medium. In other embodiments, the summer 400, the PID transfer function 402, the feedback 406, and the setpoint 408 may be implemented in software, hardware, software in execution, firmware, bytecode, microcode, PLDs, FPGAs, PALs, a microprocessor, a microcontroller, or some combination thereof.

The setpoint 408 may be a target voltage, a target current of the power signal, a target current of the electrosurgical energy, a target voltage of the power signal, or a target voltage of the electrosurgical energy (see FIG. 2). The current of the power signal may be sensed using the sense resistor 228.

The setpoint 408 is provided to the summer 400 which compares the setpoint 408 to the feedback 406. That is, the setpoint 408 is a desired or target value, and the feedback 406 provides the actual value being delivered. The feedback 406 corresponds to the setpoint 408. For example, if the setpoint 408 is a target power signal current, the feedback 406 provides a signal of the current of the power signal as measured using the sense resistor 228.

The summer 400 compares the setpoint 408 to the feedback 406 and generates an error signal. The error signal is the difference between the setpoint 408 and the feedback 406. Typically, the summer subtracts the feedback 406 from the setpoint 408 (also referred to as negative feedback). The error signal is fed into the PID transfer function 402.

The PID transfer function 402 adds proportional, integral and derivative terms together and outputs the results to the PWM driver 404 that converts the results to a PWM signal. The PWM driver 404 provides the PWM signal to the power supply 204. Each term includes a coefficient. Specifically, the proportional term is the error signal multiplied by a proportional coefficient, the integral term is the integration of the error signal multiplied by an integral coefficient, and the derivative term is the derivative of the error signal multiplied by a derivative coefficient. As previously mentioned, the proportional, integral, and derivative terms are added together and sent to the PWM driver 404. Although FIG. 4 shows the output of the PID transfer function 402 as being sent directly to a PWM driver 404 to generate the PWM signal, various other driver circuitry may be used (e.g., an analog-to-digital converter (not explicitly shown), etc.).

Figure 5A:
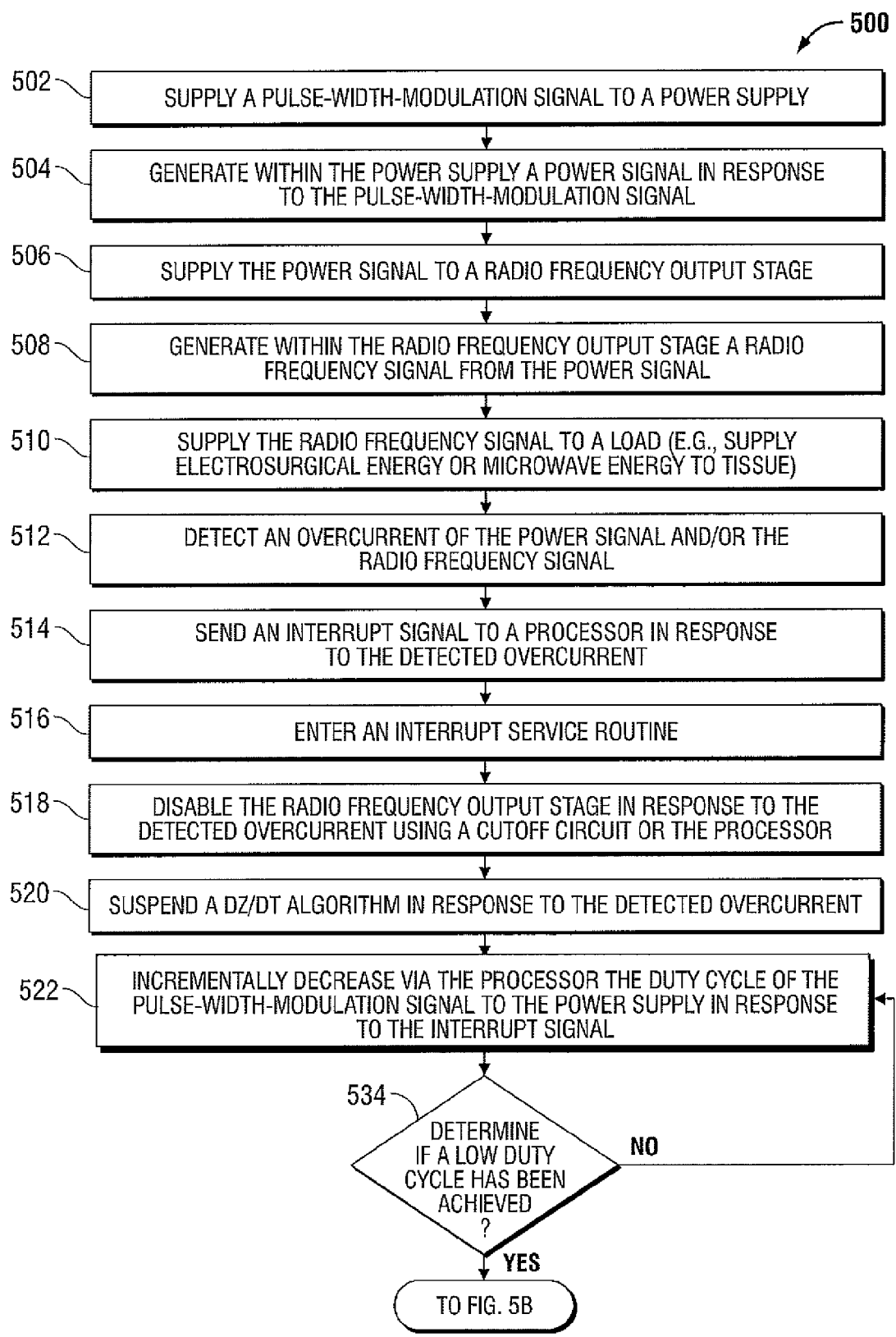
FIGS. 5A and 5B show a flowchart illustrating a method for mitigating overcurrent conditions according to an embodiment of the present disclosure.
Figure 5B:
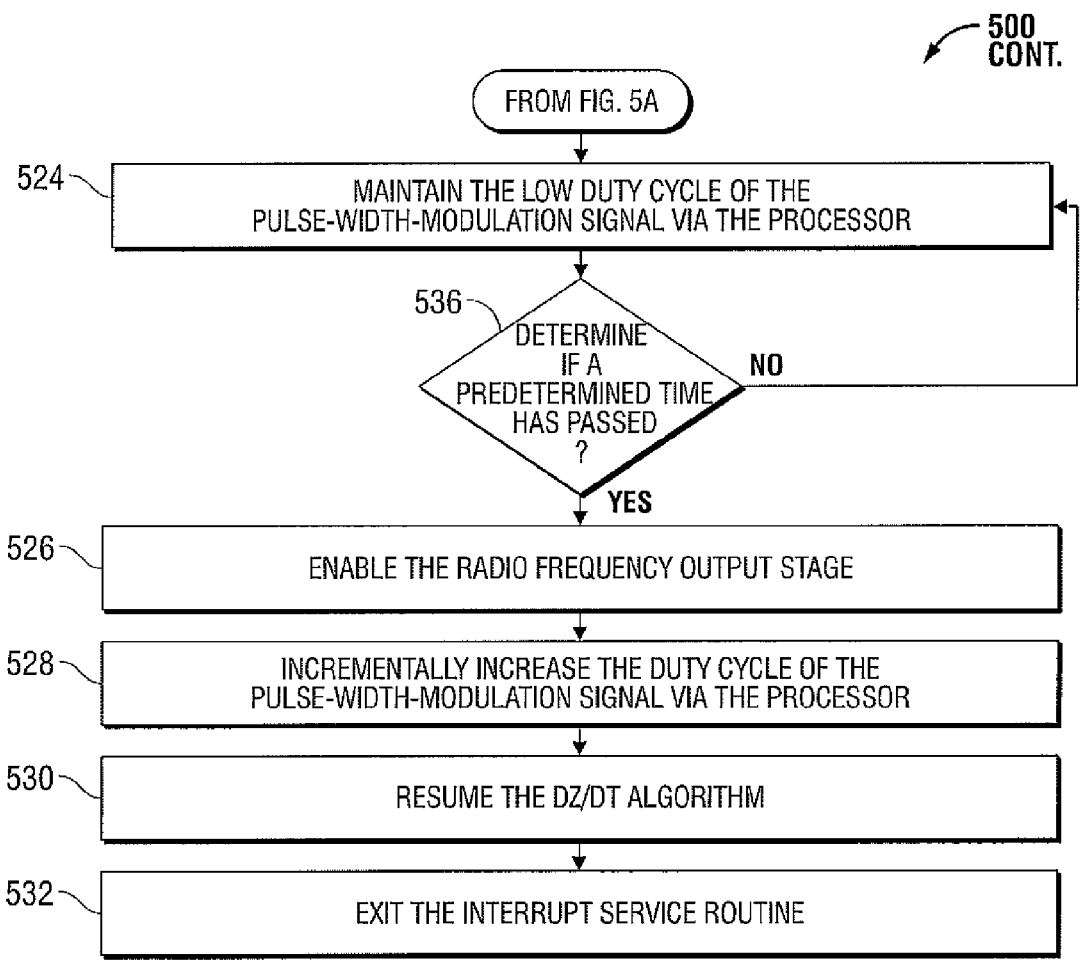

Referring now to FIGS. 2, 5A and 5B. FIGS. 5A and 5B show a flowchart illustrating a method 500 for mitigating overcurrent conditions according to an embodiment of the present disclosure. The method 500 may be performed by the electrosurgical generator 102 according to one embodiment of the present disclosure. Method 500 includes steps 502-532 and decisions 534-536.

Step 502 supplies a pulse-width modulation signal to a power supply, e.g., the controller 202 supplies the power supply 204 with the pulse-width modulation signal. Step 504 generates within the power supply a power signal in response to the pulse-width modulation signal. Step 506 supplies the power signal to a radio frequency output stage. For example, the power supply 204 supplies the power signal to the radio frequency output stage as shown in FIG. 2.

Step 508 generates within the radio frequency output stage a radiofrequency signal, e.g., electrosurgical energy, from the power signal. Step 510 supplies the radio frequency signal to a load, e.g., step 510 supplies electrosurgical energy or microwave energy to tissue.

Step 512 detects an overcurrent of the power signal or the radio frequency signal. For example, the overcurrent detection circuit 210 detects an overcurrent of the power signal from the power supply 204 or an overcurrent of the electrosurgical energy from the RF output stage 206.

Step 514 sends an interrupt signal to a processor in response to the detected overcurrent and at step 516, and the processor enters into an interrupt service routine, such as the ISR 222 of FIG. 2. Step 518 disables the radio frequency output stage in response to the detected overcurrent using a cutoff circuit or the processor disable the radio frequency output stage (see the OR gate 220 of FIG. 2).

Step 520 suspends a dz/dt algorithm in response to the detected overcurrent. The electrosurgical generator 102 provides electrosurgical energy and controls for the derivative of tissue impedance over dt. A description of the dz/dt algorithm may be found in commonly assigned U.S. Pat. No. 7,972,328 to Robert H. Wham et al., the disclosure of which is incorporated herein by reference in its entirety.

Step 522 incrementally decreases via the processor the duty cycle of the pulse-width modulation signal to the power supply in response to the interrupt signal. For example, when the electrosurgical generator 102 detects an overcurrent, the RF output stage 206 may be quickly disabled because the switches 216 disconnect the PWM1 and PWM2 signals. Shortly thereafter, or simultaneously, the controller 202 incrementally decreases the PWM signal to the power supply 204. For example, the controller 202 may decrease the duty cycle by 10% after a predetermined number of pulses are sent to the power supply 204 or after a predetermined amount of time.

At decision step 534, the method 500 determines if a low duty cycle has been achieved. The low duty cycle may be predetermined. For example, the low duty cycle may be the duty cycle at which the power signal from the power supply 204 is slightly beyond a threshold such that the RF output stage 206 can supply enough electrosurgical energy for the sensors 208 to measure the electrosurgical energy. Additionally or alternatively, the low duty cycle may be slightly above the amount needed so that the voltage, current, and/or power of the power signal can be measured by the overcurrent detection circuit 210.

Once the low duty cycle has been achieved, step 524 maintains the low duty cycle of the pulse-width modulation signal via the processor. Decision step 536 determines if a predetermined time has passed. After the predetermined time has passed at decision step 536, step 526 enables the radio frequency output stage. Step 528 incrementally increases the duty cycle of the pulse-width modulation signal via the processor. Step 530 resumes the dz/dt algorithm. Step 532 exits the interrupt service routine.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method for mitigating overcurrent conditions, comprising the steps of:
    supplying a pulse-width modulation signal to a power supply;
    generating within the power supply a power signal in response to the pulse-width modulation signal;
    supplying the power signal to a radio frequency output stage;
    generating within the radio frequency output stage a radio frequency signal from the power signal;
    supplying the radio frequency signal to a load;
    detecting an overcurrent of at least one of the power signal and the radio frequency signal;
    sending an interrupt signal to a processor in response to the detected overcurrent;
    disabling the radio frequency output stage in response to the detected overcurrent; and
    incrementally decreasing, via the processor, a duty cycle of the pulse-width modulation signal to the power supply in response to the interrupt signal while the duty cycle of the pulse-width modulation signal is above a predetermined low duty cycle.

2. The method according to claim 1, wherein the processor disables the radio frequency output stage in response to the detected overcurrent.

3. The method according to claim 1, wherein disabling the radio frequency output stage in response to the detected overcurrent includes disabling the radio frequency output stage using a cutoff circuit in response to the detected overcurrent.

4. The method according to claim 1, further comprising maintaining, by the processor, the predetermined low duty cycle of the pulse-width modulation signal for at least a predetermined time.

5. The method according to claim 4, further comprising enabling the radio frequency output stage after the predetermined time.

6. The method according to claim 5, further comprising incrementally increasing, via the processor, the duty cycle of the pulse-width modulation signal after the predetermined time.

7. The method according to claim 1, further comprising setting, via an interrupt service routine, a setpoint of a control system to control the power supply to maintain a low duty cycle of the pulse-width modulation signal for at least a predetermined time.

8. The method according to claim 1, further comprising causing the processor to enter into a recovery state or execute an interrupt service routine in response to the interrupt signal.

9. The method according to claim 1, wherein the radio frequency output stage includes two driving transistors coupled to a transformer in a push-pull configuration, and
    wherein the disabling of the radio frequency output stage includes disabling driving signals to the two driving transistors.

10. The method according to claim 1, further comprising suspending a dz/dt algorithm in response to the detected overcurrent.

* * * * *